(12) United States Patent
Wang et al.

(10) Patent No.: US 8,167,845 B2
(45) Date of Patent: May 1, 2012

(54) CATHETER HAVING DISTAL SEALING MEMBER

(75) Inventors: Huisun Wang, Maple Grove, MN (US); Dale Just, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 368 days.

(21) Appl. No.: 12/476,539

(22) Filed: Jun. 2, 2009

(65) Prior Publication Data
US 2010/0305423 A1  Dec. 2, 2010

(51) Int. Cl.
*A61M 5/178* (2006.01)
(52) U.S. Cl. .............. 604/167.06; 604/167.01
(58) Field of Classification Search ........... 604/167.01, 604/167.06, 192, 198, 264, 533–539; 607/101–105; 606/41; 600/372–395
See application file for complete search history.

(56) References Cited

U.S. PATENT DOCUMENTS

| | | | |
|---|---|---|---|
| 5,122,123 A * | 6/1992 | Vaillancourt | ............... 604/192 |
| 6,939,309 B1 | 9/2005 | Beatty et al. | |
| 6,990,370 B1 | 1/2006 | Beatty et al. | |
| 7,123,959 B2 | 10/2006 | Cates | |
| 7,142,912 B2 | 11/2006 | Wagner et al. | |
| 7,189,208 B1 | 3/2007 | Beatty et al. | |
| 7,229,469 B1 | 6/2007 | Witzel et al. | |
| 7,291,146 B2 * | 11/2007 | Steinke et al. | ............... 606/41 |
| 2003/0028118 A1 | 2/2003 | Dupree et al. | |
| 2003/0069570 A1 | 4/2003 | Witzel et al. | |
| 2005/0222632 A1 | 10/2005 | Obino | |
| 2006/0041232 A1 * | 2/2006 | Stearns et al. | ........... 604/167.06 |
| 2007/0179543 A1 | 8/2007 | Ben-David et al. | |
| 2007/0244479 A1 | 10/2007 | Beatty et al. | |
| 2008/0091191 A1 | 4/2008 | Witzel et al. | |
| 2008/0177338 A1 | 7/2008 | Ben-David et al. | |
| 2008/0183076 A1 | 7/2008 | Witte et al. | |
| 2008/0234564 A1 | 9/2008 | Beatty et al. | |

\* cited by examiner

*Primary Examiner* — Linda Dvorak
*Assistant Examiner* — Brian M Antiskay
(74) *Attorney, Agent, or Firm* — Armstrong Teasdale LLP

(57) ABSTRACT

A catheter includes a proximal end, a distal end, a tubular member, and an inner member extending through the tubular member. The inner member is movable axially relative to the tubular member. The catheter also includes a seal member including a first portion and a second portion. The seal member extends between the tubular member and the inner member. The first portion of the seal member remains stationary relative to the tubular member, and the second portion of the seal member remains stationary relative to the inner member during relative axial movement between the tubular member and the inner member.

12 Claims, 5 Drawing Sheets

CATHETER HAVING DISTAL SEALING MEMBER

BACKGROUND OF THE INVENTION

1. Field of the Invention

The field of the invention relates generally to catheters and, more specifically, to catheters having seals located in a distal portion thereof that prevent fluid passage during a surgical procedure.

2. Background Art

During surgical procedures that utilize a catheter, controlling fluid passage through the catheter is important. It is particularly important when the catheter includes inner channels that extend the length of the catheter and have physical elements passing therethrough. For example, as illustrated in FIG. 1, a known basket electrode mapping catheter 100 includes a first inner tube or rod member 102 that passes through a second outer tubular member 104. As basket electrode 106 is extended and retracted, relative movement occurs between members 102 and 104. To allow such relative movement, a space or gap 108 exists between members 102 and member 104. It is through spaces, such as gap 108, that blood and other bodily fluids can flow 110 unless they are impeded.

BRIEF DESCRIPTION OF THE INVENTION

In one aspect, a catheter is provided that includes a proximal end, a distal end, a tubular member, and an inner member extending through the tubular member. The inner member is movable axially relative to the tubular member. The catheter also includes a seal member including a first portion and a second portion. The seal member extends between the tubular member and the inner member. The first portion of the seal member remains stationary relative to the tubular member, and the second portion of the seal member remains stationary relative to the inner member during relative axial movement between the tubular member and the inner member.

In another aspect, a basket electrode mapping catheter is provided that includes a proximal end, a distal end, a tubular member, an inner member extending through the tubular member, and a basket electrode connected to a distal end of the inner member. The catheter also includes a seal member having a first portion and a second portion. The seal member first portion contacts the tubular member. The seal member second portion contacts the inner member. The seal member is configured to prevent fluid flow between the tubular member and the inner member.

BRIEF DESCRIPTION OF THE DRAWINGS

FIG. 3A is an enlarged view of the collar shown in FIG. 3.

DETAILED DESCRIPTION OF THE INVENTION

The invention set forth below in detail is a sealed catheter having a mapping electrode assembly that is utilized, for example, in an electrophysiology procedure. In one embodiment, the catheter includes an inner member such as an inner tubular member, or a rod that moves axially with respect to an outer tubular member. The catheter also includes a seal that includes a portion that remains stationary relative to the inner member during at least a portion of the movement of the inner member. In addition, the seal includes a portion that remains relatively stationary with the outer tubular member during at least a portion of the movement of the inner member.

The systems and methods set forth below are not limited to the specific embodiments described herein. In addition, components of each system and steps of each method can be practiced independently and separately from other components and method steps described herein. Each component and method step also can be used in combination with other catheters, electrodes, systems, and methods.

As used herein, "proximal" refers to the direction away from the body of a patient and towards a clinician. Furthermore, as used herein, "distal" refers to the direction toward the body of a patient and away from the clinician.

Figure 1:
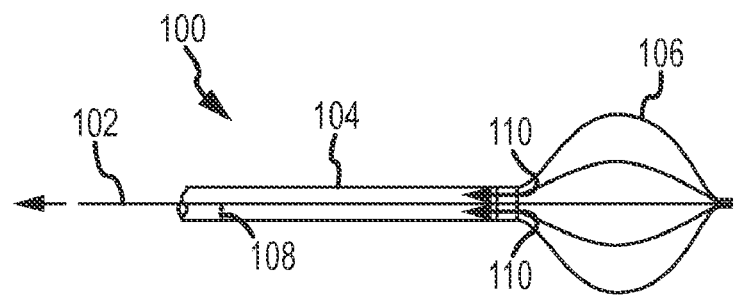
FIG. 1 is a schematic view of a prior art basket electrode mapping catheter showing potential fluid ingress into the catheter.
Figure 2:
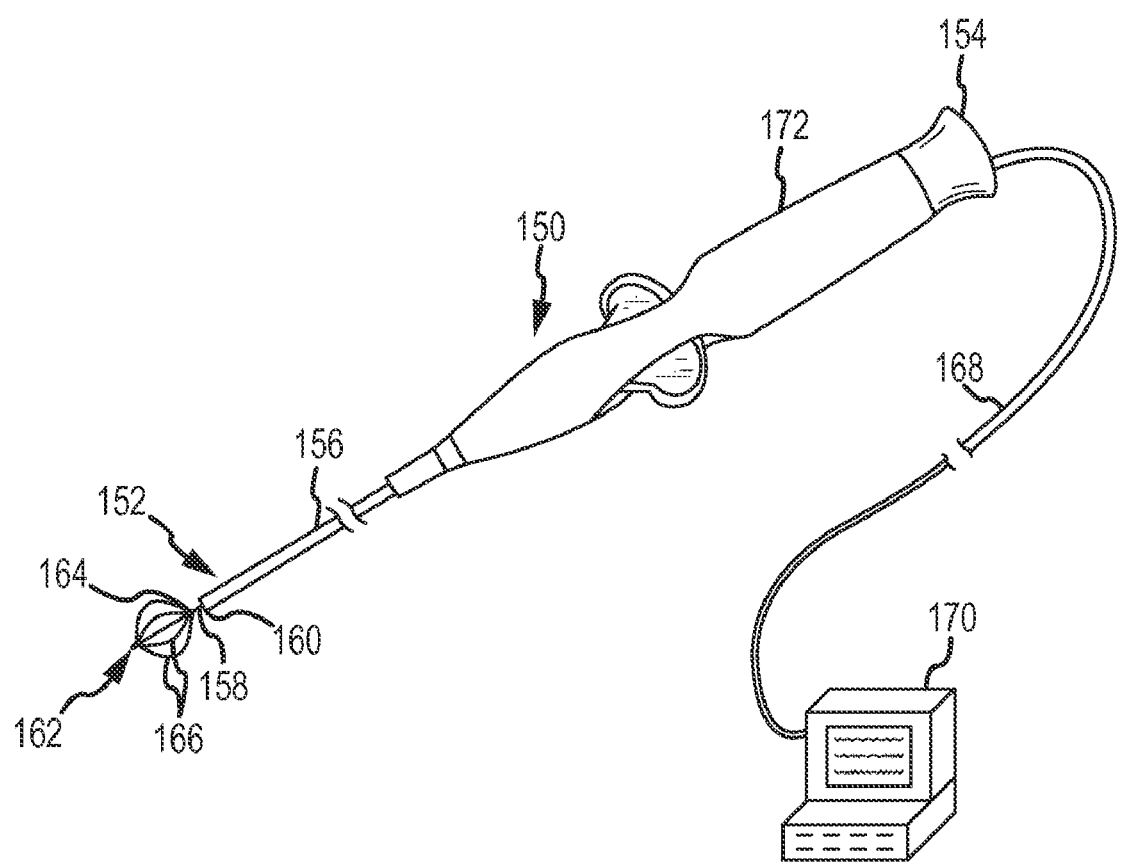
FIG. 2 is a schematic view of a basket electrode mapping catheter in accordance with one embodiment of the invention.

FIG. 2 is a schematic view of a basket electrode mapping catheter 150 in accordance with one embodiment of the present invention. While FIG. 2 is shown with a basket electrode mapping catheter, other mapping catheters are within the scope of this invention, including circular mapping catheters lariat designs, splines, and the like. Catheter 150 includes a distal end 152 and a proximal end 154. An outer tubular member 156 extends from distal end 152 to proximal end 154. An inner member 158 extends through outer tubular member 156 and is at least partially extendable beyond a distal end 160 of outer tubular member 156. A basket electrode assembly 162 is connected to a distal end 164 of inner member 158. In one embodiment, inner member 158 is a rod. In another embodiment, inner member 158 is a tubular member. Basket electrode assembly 162 includes a plurality of arms 166, each including at least one electrode (not shown in FIG. 2). A set of leads (not shown) extend from the electrodes through outer tubular member 156. The leads extend from catheter proximal end 154 in a cable 168 that is connected to an EKG recording system, such as EP-Workmate® EP Lab Recording System, or EnSite® System.

Catheter 150 also includes a handle 172 at proximal end 154. Handle 172 is utilized to manipulate catheter distal end 152, and more specifically, basket electrode assembly 162, during operation of catheter 150.

Figure 3:
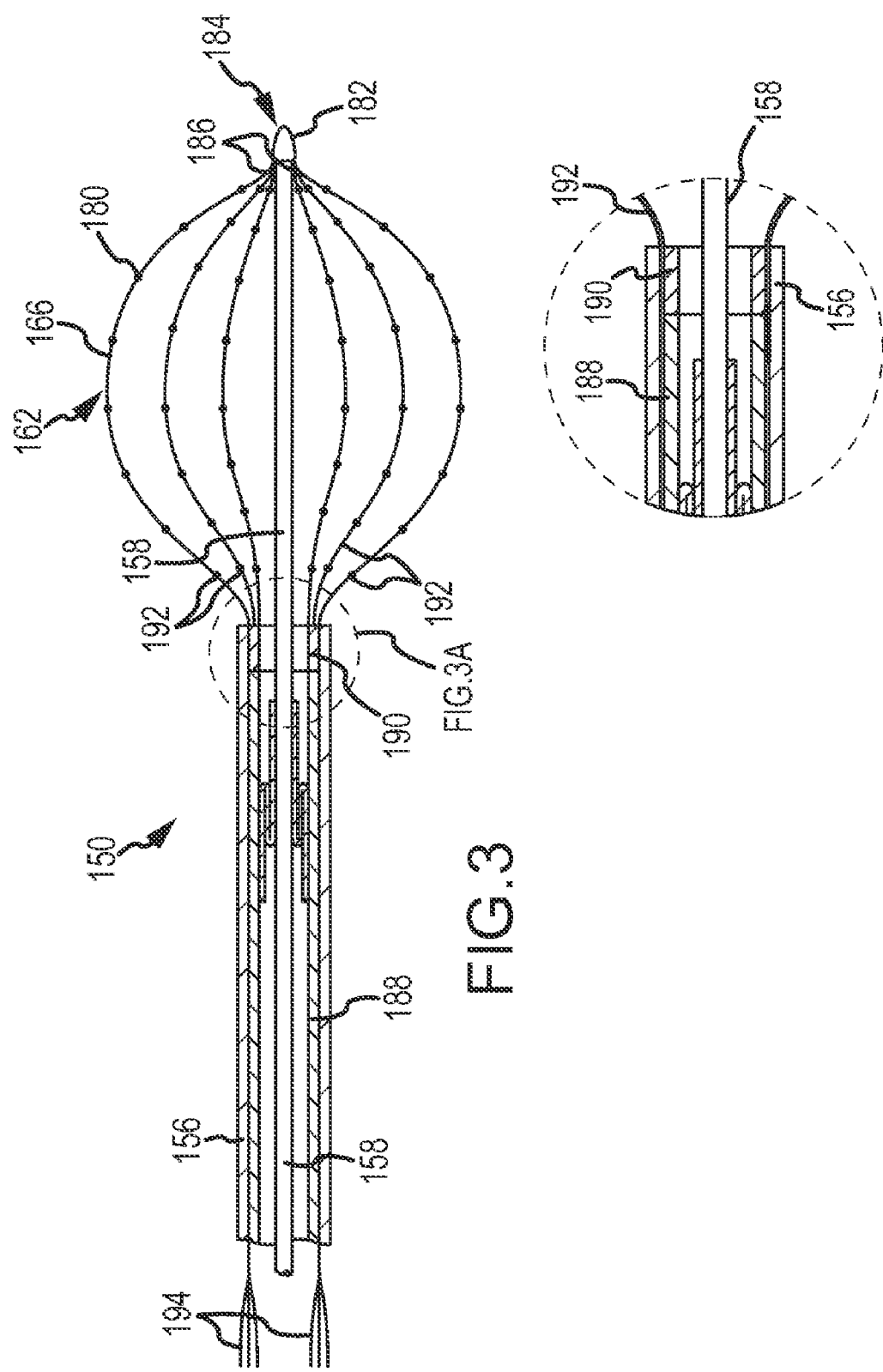
FIG. 3 is a schematic view of the basket electrode shown in FIG. 2 including a collar.

FIG. 3 is a schematic view of basket electrode assembly 162 extended from outer tubular member 156. Assembly 162 includes a plurality of electrode arms 166, each including a plurality of electrodes 180. Inner member 158 forms a central shaft through basket electrode assembly 162. Assembly 162 includes a cap 182 at a distal tip 184 of inner member 158. Cap 182 is utilized to contain distal ends 186 of arms 166 and is fabricated from a soft polymer such as polyurethane or silicone. Assembly 162 also includes a middle tubular member 188 positioned between outer tubular member 156 and inner member 158. A collar 190 is used to attach proximal ends 192 of arms 166 to middle tubular member 188. As shown in FIG. 3A, proximal ends 192 of arms 166 pass through collar 190 and are attached to middle tubular member 188 by collar 190. A set of wires 194 extends proximally from collar 190 and, in one embodiment, is connected to EKG recording system 170 (shown in FIG. 2).

FIG. 3 also illustrates a seal member 200 attached to inner member 158 and middle tubular member 188. Seal member 200 is configured to prevent fluid flow between inner member 158 and middle tubular member 188, while still enabling relative axial movement between inner member 158 and middle tubular member 188. In one embodiment, basket assembly 162 is extended from outer tubular member 156 through distal movement of both inner member 158 and middle tubular member 188. Once inner member 158 has been extended the proper amount, middle tubular member 188 is further extended to bend electrode arms 166 and force them away from inner member 158 and into contact with an interior surface of a heart. Since inner members are formed from resilient material, they are able to apply varying forces to the heart tissue depending on the amount of distance between cap 182 and collar 190. Catheter 150 can allow for unimpeded blood flow through the heart during the procedure while placing electrodes 180 into contact with a heart chamber wall for in-contact mapping of the physiologic potentials of the heart. In the alternative, catheter 150 can further include a balloon (not shown) to exclude blood flow between arms 166.

Figure 4:
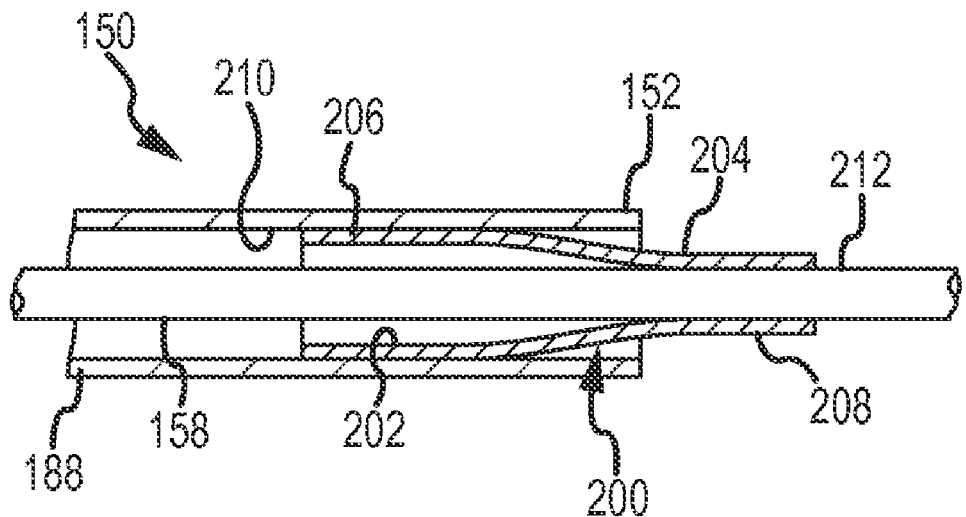
FIG. 4 is a cut-away view of a seal used in the catheter shown in FIG. 2 with the inner member in an extended position.
Figure 5:
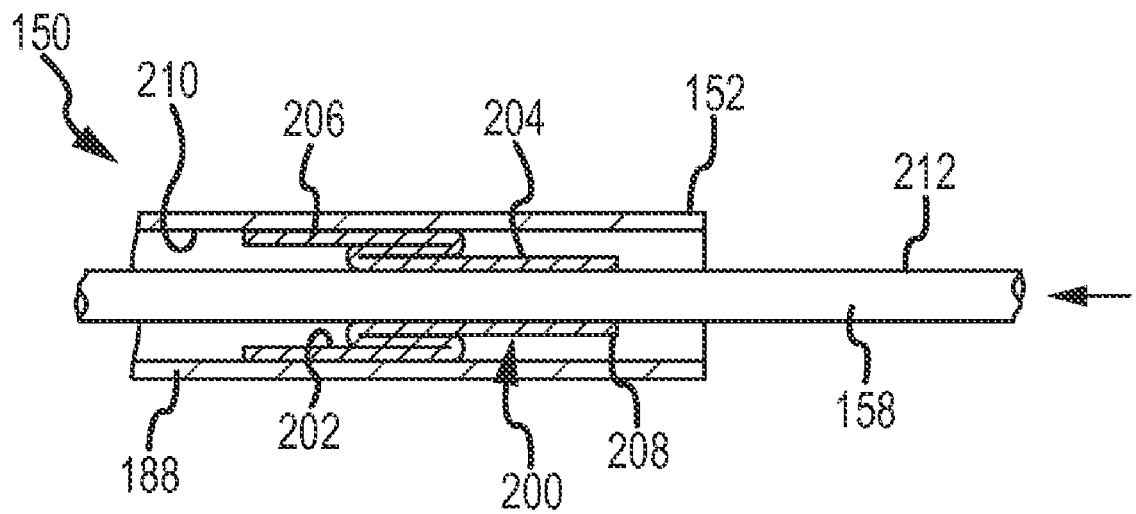
FIG. 5 is a cut-away view of the seal shown in FIG. 4 with the inner member in a retracted position.

FIGS. 4 and 5 are cut-away views of distal end 152 of catheter 150 including a seal member 200. FIGS. 4 and 5 are directed to seal member 200 that extends between middle tubular member 188 and inner member 158. As such, some of the details of catheter 150 shown in FIG. 3 have been removed for clarity. It should be understood, however, that FIGS. 4 and 5 illustrate a specific aspect of catheter 150 shown in FIG. 3.

Seal member 200 includes an inner surface 202 and an outer surface 204. In addition, seal member 200 includes a first portion 206 and a second portion 208. Outer surface 204 of seal member first portion 206 contacts and is attached to an inner surface 210 of middle tubular member 188, and inner surface 202 of seal member second portion 208 contacts and is attached to an outer surface 212 of inner member 158. In one embodiment, portions 206 and 208 are attached to members 188 and 158, respectively, with an adhesive. Alternatively, portions 206 and 208 are attached to members 188 and 158, respectively, with a mechanical fastener. Seal member 200 is placed between the two catheter portions that must be sealed, e.g., between middle tubular member 188 and inner tubular member 158, or between middle tubular member 188 and outer tubular member 156.

As shown in FIGS. 4 and 5, seal member 200 is a tubular member that surrounds inner member 158 and is at least partially contained within middle tubular member 188. During extension of inner member 158, second portion 208 of seal member 200 moves distally with respect to first portion 206. FIG. 4 illustrates inner member 158 in a fully extended configuration and FIG. 5 illustrates inner member 158 in a fully retracted configuration and shows seal member 200 folded upon itself. Seal member 200 is configured to prevent fluid ingress through the space between middle tubular member 188 and inner member 158 while allowing inner member 158 to move a sufficient amount so that basket electrode 162 (shown in FIGS. 2 and 3) can be fully deployed during a procedure and fully retracted when not is use, or vice versa. In one embodiment, seal member 200 is fabricated from at least one of polyurethane, silicone, and any other suitable biocompatible material that is flexible and fluid impermeable.

Figure 6:
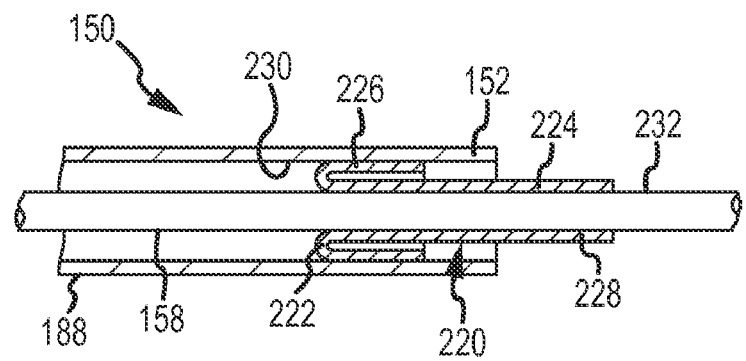
FIG. 6 is a cut-away view of an alternative seal used in the catheter shown in FIG. 2.
Figure 7:
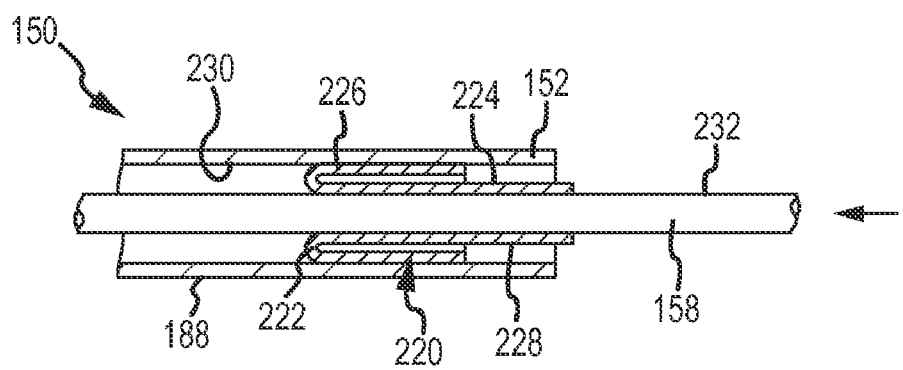
FIG. 7 is a cut-away view of a further alternative seal used in the catheter shown in FIG. 2.

FIGS. 6 and 7 are cut-away views of distal end 152 of catheter 150 including an alternative seal member 220. FIGS. 6 and 7 are directed to seal member 220 that extends between middle tubular member 188 and inner member 158. As such, some of the details of catheter 150 shown in FIG. 3 have been removed for clarity. It should be understood, however, that FIGS. 6 and 7 illustrate an alternative aspect of catheter 150 shown in FIG. 3.

Seal member 220 extends between middle tubular member 188 and inner member 158. Seal member 220 includes a first surface 222 and a second surface 224. In addition, seal member 220 includes a first portion 226 and a second portion 228. First surface 222 of seal member first portion 226 contacts and is attached to an inner surface 230 of middle tubular member 188. First surface 222 of seal member second portion 228 also contacts and is attached to an outer surface 232 of inner member 158. In one embodiment, portions 226 and 228 are attached to members 188 and 158, respectively, with an adhesive. Alternatively, portions 226 and 228 are attached to members 188 and 158, respectively, with a mechanical fastener.

As shown in FIGS. 6 and 7, seal member 220 is a tubular member that surrounds inner member 158 and is at least partially contained within middle tubular member 188. During extension of inner member 158, second portion 228 of seal member 220 moves distally with respect to first portion 226. FIG. 6 illustrates inner member 158 in a fully extended configuration and FIG. 7 illustrates inner member 158 in a fully retracted configuration and shows seal member 220 folded upon itself. Seal member 220 is configured to prevent fluid ingress through the space between middle tubular member 188 and inner member 158 while allowing inner member 158 to move a sufficient amount so that basket electrode 162 (shown in FIGS. 2 and 3) can be fully deployed during a procedure and fully retracted when not is use. In one embodiment, seal member 220 is fabricated from at least one of polyurethane, silicone, and any other suitable biocompatible material that is flexible and fluid impermeable.

Figure 8:
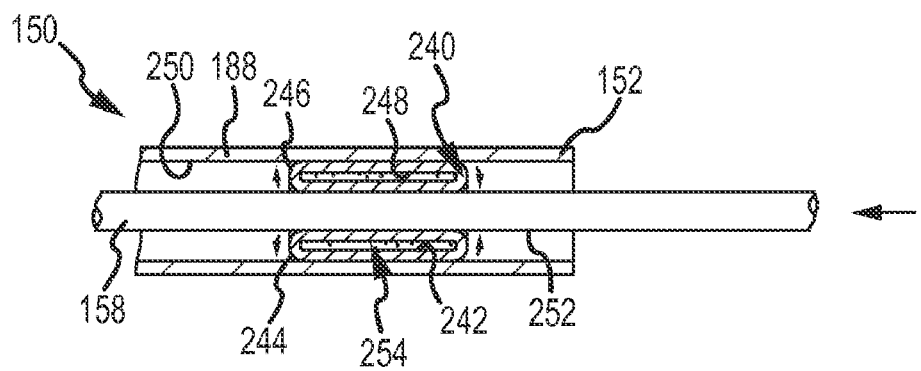
FIG. 8 is a cut-away view of a rolling seal used in the catheter shown in FIG. 2.

FIG. 8 is a cut-away view of distal end 152 of catheter 150 including an alternative seal member 240. As shown in FIG. 8, seal member 240 extends between middle tubular member 188 and inner member 158. As such, some of the details of catheter 150 shown in FIG. 3 have been removed for clarity. It should be understood, however, that FIG. 8 illustrates a specific alternative aspect of catheter 150 shown in FIG. 3.

Seal member 240 is a rolling seal that extends between middle tubular member 188 and inner member 158. Seal member 240 includes an inner surface 242 and an outer surface 244. In addition, seal member 200 includes a first portion 246 and a second portion 248. Outer surface 244 of seal member 240 contacts an inner surface 250 of middle tubular member 188 and an outer surface 252 of inner member 158. In one embodiment, outer surface 244 of seal member 240 is not attached to either middle tubular member 188 or inner member 158, but rather is held stationary with regard to inner surface 250 and outer surface 252 with friction between surfaces 244, 250, and 252.

As shown in FIG. 8, seal member 240 is a ring member that surrounds inner member 158 and is at least partially contained within middle tubular member 188. Seal member 240 is thus able to move with a rolling motion during relative movement between middle tubular member 188 and inner member 158. Seal member 240 is configured to prevent fluid ingress through the space between middle tubular member 188 and inner member 158 while allowing inner member 158 to move a sufficient amount so that basket electrode 162 can be fully deployed during a procedure and fully retracted when not is use.

Seal member 240 includes an inner chamber 254 that contains a fluid. In one embodiment, the fluid is at least one of a gas, such as $CO_2$, and a liquid such as silicone gel, water, saline solution, and other biocompatible materials. In one embodiment, seal member 240 is fabricated from at least one of polyurethane, silicone, and any other suitable biocompatible material that is flexible and fluid impermeable.

Figure 9:
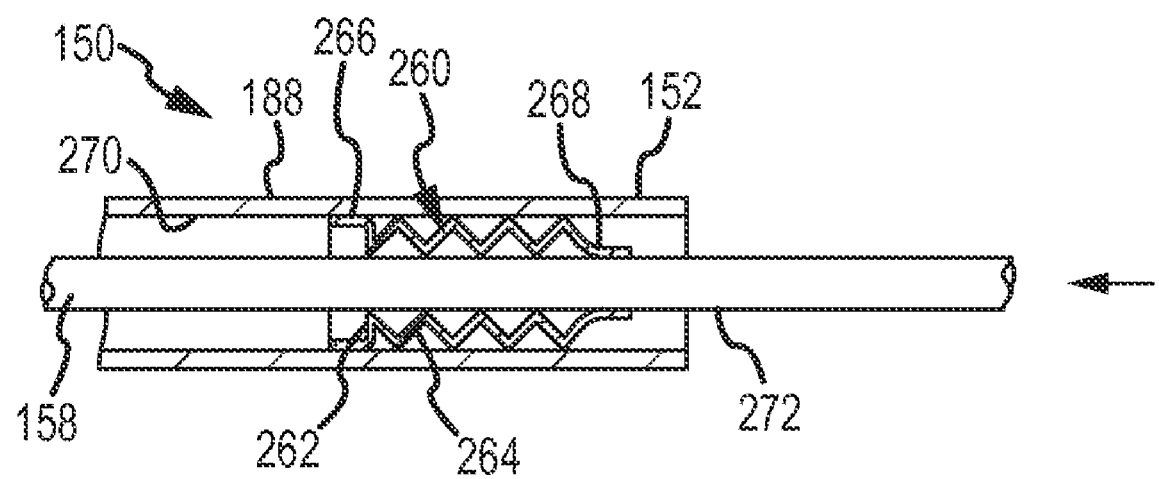
FIG. 9 is a cut-away view of an accordion seal used in the catheter shown in FIG. 2.

FIG. 9 is a cut-away view of distal end 152 of catheter 150 including a further alternative seal member 260. FIG. 9 is directed to seal member 260 that extends between middle tubular member 188 and inner member 158. As such, some of the details of catheter 150 shown in FIG. 3 have been removed for clarity. It should be understood, however, that FIG. 9 illustrates a specific alternative aspect of catheter 150 shown in FIG. 3.

Seal member 260 extends between middle tubular member 188 and inner member 158. Seal member 260 includes an inner surface 262 and an outer surface 264. In addition, seal member 260 includes a first portion 266 and a second portion 268. Outer surface 264 of seal member first portion 266 contacts and is attached to an inner surface 270 of middle tubular member 188, and inner surface 262 of seal member second portion 268 contacts and is attached to an outer surface 272 of inner member 158. In one embodiment, portions 266 and 268 are attached to members 188 and 158, respectively, with an adhesive. Alternatively, portions 266 and 268 are attached to members 188 and 158, respectively, with a mechanical fastener.

As shown in FIG. 9, seal member 260 is a tubular member that surrounds inner member 158 and is at least partially contained within middle tubular member 188. During extension of inner member 158, second portion 268 of seal member 260 moves distally with respect to first portion 266. FIG. 9 illustrates inner member 158 in a fully retracted configuration and shows seal member 260 folded upon itself. Seal member 260 is configured to prevent fluid ingress through the space between middle tubular member 188 and inner member 158 while allowing inner member 158 to move a sufficient amount so that basket electrode assembly 162 (shown in FIGS. 2 and 3) can be fully deployed during a procedure and fully retracted when not is use. In one embodiment, seal member 260 is fabricated from at least one of polyurethane, silicone, and any other suitable biocompatible material that is flexible and fluid impermeable.

Catheter 150 is utilized by inserting distal end 152 into a patient's vascular system and maneuvering distal end to an appropriate location within a patient's heart. Once distal end 152 is properly positioned, handle 172 is manipulated so that basket electrode assembly 162 is extended beyond outer tubular member distal end 160. Basket electrode assembly 162 is moved distally beyond outer tubular member 156 by distal movement of middle tubular member 188 and inner member 158. Once basket electrode assembly 162 is extended beyond outer tubular member 156, the movement of inner member 158 is stopped while middle tubular member 188 is further extended distally, thus bending electrode arms 166 radially outwardly. Basket electrode assembly 162 is then maneuvered to properly position electrodes 180 and energy is applied to electrodes 180 so that an electric field is created in the heart. Readings are taken and information is processed so that, for example, a proper reading of the heart is obtained. Basket electrode assembly 162 is retracted into outer tubular member 156 and catheter 150 is then removed from the patient's vascular system.

Exemplary embodiments of catheters, electrode assemblies, and methods of assembly are described in detail above. The catheter, electrode assemblies, and methods are not limited to the specific embodiments described herein, but rather, components of the catheter and electrode assembly and/or steps of the methods may be utilized independently and separately from other components and/or steps described herein. It is noted that the exemplary embodiments can be implemented and utilized in connection with many other ablation applications.

Although specific features of various embodiments of the invention are shown in some figures and not in others, this is for convenience only. In accordance with the principles of the invention, any feature of a figure may be referenced and/or claimed in combination with any feature of any other figure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. For example, although a three member catheter with a distal seal located between two of the members is described above, it should be understood that any number of tubes can be utilized in the catheter as long as a seal is positioned between, and contacts, two longitudinally extending members.

What is claimed is:

1. A catheter comprising:
a proximal end;
a distal end;
a tubular member;
an inner member extending through said tubular member, said inner member movable axially relative to said tubular member; and
a seal member comprising a first portion and a second portion, said seal member extending between said tubular member and said inner member, said first portion of said seal member remaining stationary relative to said tubular member and said second portion of said seal member remaining stationary relative to said inner member during relative axial movement between said tubular member and said inner member.

2. A catheter in accordance with claim 1 wherein said inner member comprises at least one of a rod and a second tubular member.

3. A catheter in accordance with claim 1 wherein said seal member first portion is attached to an inner surface of said tubular member.

4. A catheter in accordance with claim 1 wherein said seal member second portion is attached to an outer surface of said inner member.

5. A catheter in accordance with claim 1 wherein said seal member comprises a first surface and a second surface, said seal member first portion attached to said tubular member at said first surface, said seal member second portion attached to said inner member at said second surface.

6. A catheter in accordance with claim 1 further comprising an outer tubular member, said inner member comprises an inner tubular member, said catheter further comprising a basket electrode assembly connected to a distal end of said inner tubular member and configured to be extended from, and retracted into, said outer tubular member.

7. A catheter in accordance with claim 6 wherein said seal member is configured to fold upon itself when said basket electrode is withdrawn into said outer tubular member.

8. A basket electrode mapping catheter comprising:
a proximal end;
a distal end;
a tubular member;
an inner member extending through said tubular member;
a basket electrode assembly connected to a distal end of said inner member; and
a seal member comprising a first portion and a second portion, said seal member first portion contacting said tubular member, said seal member second portion contacting said inner member, said second portion of said seal member remaining stationary relative to said inner member during relative axial movement between said tubular member and said inner member, said seal member configured to prevent fluid flow between said tubular member and said inner member.

9. A catheter in accordance with claim 8 wherein said inner member comprises at least one of a rod and a second tubular member.

10. A catheter in accordance with claim 8 wherein said seal member comprises a first surface and a second surface, said first surface of said seal member first portion contacting said tubular member, said second surface of said seal member second portion contacting said inner member.

11. A catheter in accordance with claim 8 further comprising an outer tubular member, said inner member comprises an inner tubular member, said basket electrode assembly configured to be extended from, and retracted into, said outer tubular member.

12. A catheter in accordance with claim 11 wherein said seal member is configured to fold upon itself when said basket electrode assembly is withdrawn into said outer tubular member.

* * * * *